United States Patent [19]

Oliveira et al.

[11] 4,242,096
[45] Dec. 30, 1980

[54] IMMUNOASSAY FOR ANTIGENS

[75] Inventors: Robert J. Oliveira, Maplewood; Spencer F. Silver, White Bear Lake, both of Minn.

[73] Assignee: Minnesota Mining and Manufacturing Company, Saint Paul, Minn.

[21] Appl. No.: 851,491

[22] Filed: Nov. 14, 1977

[51] Int. Cl.² ............................................. G01N 33/16
[52] U.S. Cl. ................................... 23/230 B; 310/312; 324/71 R; 422/57; 422/61; 422/69; 424/12
[58] Field of Search .................... 23/230 B; 73/61.1 R; 310/312; 424/12; 422/57, 61, 69; 324/71 R

[56] References Cited
U.S. PATENT DOCUMENTS 4,054,646  10/1977  Giaever ............................. 23/230 B

OTHER PUBLICATIONS

Shons et al., J. Biomed. Mater. Res., 6, 565 (1972).

*Primary Examiner*—Sidney Marantz
*Attorney, Agent, or Firm*—Cruzan Alexander; Donald M. Sell; Carolyn A. Bates

[57] ABSTRACT

An improved indirect assay and article for determining an antigen in a liquid sample. The assay utilizes a piezoelectric oscillator which has been coated with the antigen or a protein mixture containing the antigen being determined. The antigen-coated oscillator is contacted with the liquid sample and a predetermined amount of an antibody specific for the antigen being determined. The amount of free antigen in the sample, if any, can be determined by measuring the change in frequency of the oscillator following contact with the liquid sample and the antibody, and referring to a standard curve.

15 Claims, 2 Drawing Figures

IMMUNOASSAY FOR ANTIGENS

This invention relates to a method and an article for the competitive assay of antigens and antigen-like substances. More particularly, the invention relates to a gravimetric immunoassay utilizing an antigen-precoated piezoelectric oscillator.

Generally, the term "antigen" is applied to any foreign substance which, when present in a host animal, will stimulate the production of specific antibodies to the substance. Antibodies show a remarkable ability to bind selectively the antigen which stimulated their production. This ability of antibodies to discriminate between antigens which stimulated their production and the myriad of other compounds of similar structure that are found in biological fluids, e.g. serum or urine, is the basis for virtually all immunoassay techniques.

A number of competitive binding assays are known in the art for the qualitative and quantitative determination of antigens and antibodies. These assays are based on the principle that when a binding element X (antigen or antibody) is mixed with a substance Y for which it has specific binding sites (corresponding antibody or antigen), a complex XY will be formed. Similarly, a form of the substance Y', which has been labeled in some manner to distinguish it from Y, without disturbing its binding affinity for X, will form a complex XY'. If the concentrations of Y and Y' exceed the number of binding sites available on X, then they will compete with each other for binding sites in proportion to their concentrations. If the amounts of X and Y' are kept constant, then as non-labeled Y is added, it will compete more effectively with Y', and the amount of XY' complex will fall. Thus, competitive binding assays for antigens require an antibody (having specific binding sites for the antigen being assayed) and a labeled form of the antigen.

Prior art competitive binding assays for antigens generally use one of several different types of labeling systems to distinguish between the two competing forms of the antigen being measured. These systems include radioactive isotope labeling, enzyme labeling, spin labeling, and fluorescent labeling.

Assays using radioactive isotope labeling are the most generally used. In these assays the labeled antigen is distinguished from the unlabeled antigen by the presence of a radioactive isotope in the former. The amount of labeled antigen bound to the antibody or the amount free in solution can readily be determined by radioactivity measurements. Radioimmuno assays are described in U.S. Pat. Nos. 3,555,143 and 3,646,346. The primary disadvantages of assay techniques using radioactive isotope labeling include radioactivity hazards, expensive instrumentation, the necessity to modify chemically the antigen to label it, constant restandardization due to short-lived isotopes and tedious separation techniques.

Competitive binding assays utilizing enzyme labeling are described in U.S. Pat. Nos. 3,654,090, 3,791,932 and 3,850,752. For example, in U.S. Pat. No. 3,850,752, the labeled antigen is distinguished from unlabeled antigen by being covalently linked to an enzyme molecule. The enzyme-antigen conjugate must retain at least part of both its immunochemical and enzymatic activity. The binding antibody is preferably insolubilized either by crosslinking or by covalent linking to an insoluble carrier. When a given amount of insolubilized antibody is added to a liquid sample containing a known amount of antigen and an unknown amount of unlabeled antigen, the two forms of the antigen compete for the binding sites on the antibody. The concentration of unknown antigen can be measured by determining the enzymatic activity of either the liquid or solid phase.

Disadvantages associated with competitive binding assays utilizing enzyme labeling include the necessity for chemical modification of the antigen, highly specialized antisera, very precise timing during assay and reagent instability. Additionally, the assays are subject to interference from the unknown sample.

U.S. Pat. No. 3,690,834 describes a competitive binding assay utilizing spin labeling. In this assay, the labeled substance is distinguished from the unlabeled substance by the presence of a stable free radical functionality. Disadvantages of the spin labeling technique include the necessity of chemical modification of the antigen, expensive and cumbersome spin label detection systems and relatively low sensitivity.

In the prior art competitive assay discussed above, the success of the technique generally depends upon a good separation of unbound antigen (both labeled and unlabeled) from the antigen-antibody reaction products. Separation has been facilitated by attaching the antibody to a solid carrier such as particles of a water insoluble carrier (U.S. Pat. No. 3,555,143) or the interior surface of a plastic test tube (U.S. Pat. No. 3,646,346). Although these techniques offer advantages in terms of ease of separation, they suffer certain disadvantages such as loss of precision and reproducibility.

The present invention overcomes many of the disadvantages associated with prior art competitive assays for antigens. The method of the present invention can be carried out without the necessity of labeling the antigen by modifying it chemically or isotopically. Furthermore, the antibody is added to the reaction mixture in its natural state. There is no necessity to attach the antibody to a solid carrier to facilitate separation.

Piezoelectric oscillators have previously been used for the direct measurement of antibodies. In *J. Biomed. Mater. Res.*, Vol. 6, pp. 565–569 (1972) Shons et al describe coating a piezoelectric oscillator with specific proteins. The protein-coated oscillator is then placed in a sample containing an unknown quantity of the corresponding antibody to the protein. As the antibody binds to the oscillator, there is a downward shift in the frequency of the oscillator. The concentration of antibody in the sample can be calculated by reference to a standard curve. This method differs from the method of the present invention in several significant respects. Firstly, the prior art method measures the concentration of antibody in an unknown sample. No operative method is disclosed for measuring the concentration of the same antigen as is bound to the surface of the oscillator. The method described in the article is not a competitive binding assay, nor can it be utilized to measure both large and small molecules. Furthermore, the unique combination of a measuring device (or label) and separation means in a competitive assay system is not described. Further differences between the present invention and the prior art will be apparent from the description of the invention hereinbelow.

According to the present invention there is provided a method for the immunochemical determination of antigen in an unknown liquid sample. The method comprises the steps of: (1) contacting the liquid sample with a predetermined amount of an antibody specific for the antigen being determined and a composite comprising a piezoelectric oscillator having immobilized thereon, in biologically active configuration, an antigen or mixture of proteins containing the antigen to be determined, and the composite having a premeasured frequency; (2) allowing the immunochemical reaction to proceed; (3) separating the oscillator from the liquid sample; and (4) determining the change in frequency of the oscillator. This method may be used to determine the presence of a particular antigen in a liquid sample, and by reference to a standard curve, the change in frequency of the oscillator can be used to determine the amount of the antigen in the sample.

The method can be carried out simply and efficiently with relatively unsophisticated, rugged and inexpensive instrumentation. Since the competing antigen is immobilized on the oscillator, there is no necessity to modify it chemically to distinguish it from the antigen to be determined. Furthermore, the competing antigen is in the solid phase, thereby facilitating separation of the antigen-antibody reaction product from the liquid specimen. Accordingly, where prior art techniques require both labeling the antigen and immobilization of the antibody, the present invention achieves the combined result by simply immobilizing the antigen on a piezoelectric oscillator.

The disadvantages associated with labeling techniques used in conventional competitive binding assays have been overcome. Unlike the most commonly used label, i.e., radioisotopes, there is no hazardous radioactivity or decay of the label with time. There are no unstable and strongly temperature, pH and time dependent reagents as in the case of assay techniques using enzyme labeling. Nor does the method of the present invention require the exacting chemical syntheses needed to prepare spin labels.

The method of the present invention can be used in the qualitative and quantitative analysis of a variety of antigenic materials ranging from low molecular weight compounds to large macromolecules which meet the requirements of competitive assays and which can be immobilized on the oscillator. Antigens at a concentration as low as $10^{-11}$ moles/liter can be measured using the method of the present invention. For many significant small molecules, e.g. medicaments, the assay has sensitivities overlapping the range of radioimmune assays, i.e., nanograms/ml.

DESCRIPTION OF DRAWINGS

Understanding of the invention will be facilitated by reference to the accompanying drawings wherein.

Figure 1:
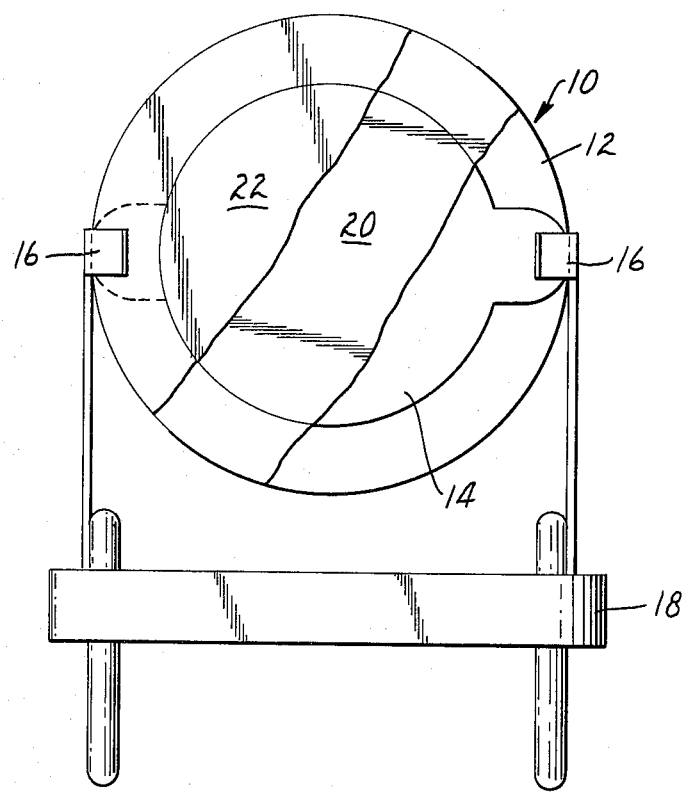
FIG. 1 is an enlarged elevational view of a piezoelectric quartz crystal oscillator partially cut away to illustrate coatings thereon.

Piezoelectric oscillators as shown in FIG. 1 are commonly used in electronic equipment as frequency standards. The term "oscillator" as used herein refers to the piezoelectric material itself which is capable of oscillating when placed in an appropriately designed electronic circuit. The oscillator 10 consists of a small quartz wafer 12 (in this case, 14 mm in diameter and 0.2 mm thick) having deposited thereon two metal electrodes 14. (The metal electrode on the opposite side of the quartz wafer 12 is not shown). Examples of metals which may be used include nickel, gold, chromium, tantalum and preferably silver. The quartz wafer 12 with electrodes 14 is supported on pins 16 on a base plug 18. When placed in an electronic oscillator circuit, the portion of quartz wafer 12 between electrodes 14 vibrates with its precise natural frequency. Preferred resonators are 5 to 10 MHz at AT-cut quartz crystals, although 1–4 MHz and 11–50 MHz crystals of similar cut may be used. A given mass mechanically coupled to one or both of the electrodes of the oscillator causes a downward shift in the fundamental or resonant frequency. Quartz crystals having a plurality of electrode pairs deposited thereon may also be used, with the portion of the crystal between each pair having a characteristic frequency. Each electrode, when coated with the same mixture of proteins, may be contacted with a different monospecific antibody, and in this way, multiple assays may be carried out using the same quartz crystal.

When used according to the present invention, the oscillator, including the electrode portion, is coated with a specific antigen layer 20. Antigen layer 20 may be immobilized directly on the electrode or a primer coat 22 may be applied to the electrode to facilitate immobilization of the antigen.

Figure 2:
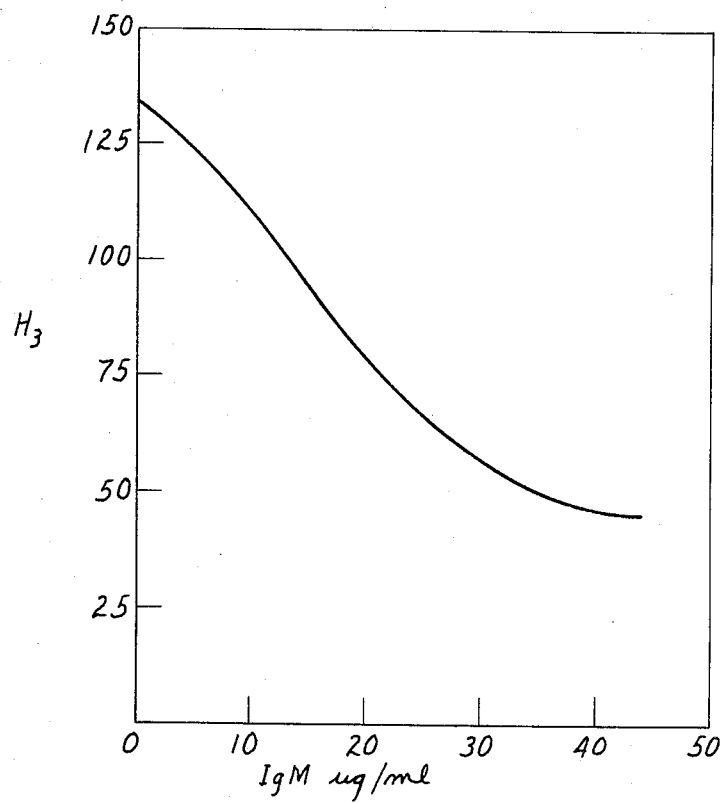
FIG. 2 is a graph illustrating a standard curve obtained by measuring the frequency changes of an antigen-coated oscillator in response to increased levels of antigen (IgM).

To practice the method of the present invention, an antigen-coated oscillator such as that illustrated in FIG. 1 having a premeasured frequency is contacted with a liquid sample, typically a biological fluid, e.g. serum or urine, containing a known concentration of antibody specific for the antigen and a known concentration of unbound antigen. Contacting the oscillator with the sample may be done by immersing the oscillator in the sample or by simply applying a drop of the mixture of antibody and sample to the surface of the electrode. Following an incubation period, generally between five minutes and two hours, and preferably between 30 and 75 minutes, the oscillator is rinsed, and its frequency is measured and recorded. By repeating this procedure, each time varying the concentration of free antigen in the sample, a standard curve can be obtained showing change in frequency as a function of free antigen concentration. A sample curve is shown in FIG. 2 for the antigen IgM. (The details of the experiment are set forth in Example 5 below). By reference to the standard curve prepared using a particular antibody the concentration of a particular antigen in an unknown sample can be readily determined.

If only one side of the oscillator is used in an assay, the reverse side can be used subsequently to assay for the same antigen or other antigens present in the antigen coat on the oscillator.

The antigen may be attached to the oscillator by a number of conventional techniques known in the art for attaching proteins to solid supports. The antigen may simply be allowed to adsorb from an aqueous solution onto the surface of the oscillator. This method is least preferred because it results in a relatively high degree of nonspecific adsorption during the assay, and sensitivity is reduced.

Similarly antigens may be deposited on hydrophobic polymer coated oscillators (such as polystyrene or fluorinated polymers) in which case attachment occurs by dispersion force interaction, which often leads to nonspecific adsorption when the surface is exposed to additional proteins, for example, during the assay.

Another technique for depositing the antigen on the oscillator is by crosslinking the protein antigen with a conventional agent such as glutaraldehyde.

An especially preferred class of immobilizing agent is described in copending application Ser. No. 851,492 filed Nov. 14, 1977, assigned to the assignee of the present application. A monolayer of these polymers applied to the surface of the oscillator promotes the deposition of a uniform layer of antigen on the oscillator. Nonspecific adsorption during the assay is minimized and a high degree of sensitivity is achieved.

The antigen is immobilized or adsorbed on the oscillator (treated or untreated) by immersing the oscillator in an aqueous solution of the antigen. A single antigen may be present in the solution, or the antigen may consist of a complex mixture of molecules. Preferred antigens include tissue-associated proteins, plasma proteins, drugs, vitamins, antibiotics, polysaccharides and nucleic acids. Optimum concentration for attachment (or adsorption) varies from antigen to antigen according to their solubility or molecular weight, however, concentrations in the range of 0.5 to 100 milligrams per milliliter are generally preferred. Attachment is accomplished preferably at room temperature and at a pH so as to maintain activity of the antigen. Optimum time for the attachment of antigens to the oscillator varies with the molecular weight and polarity of the antigen. For example, serum albumin (MW=60,000; isoelectric point 4.5) requires as little as five minutes, whereas, IgM(MW=750,000–1,000,000; isoelectric point c.a. 7.5) requires approximately 24 hours. Additionally, mixtures of proteins may be adsorbed, for example the Cohn fraction II gamma globulins or the $\alpha$-globulin fraction of serum, in which case several different types of proteins are attached simultaneously. Since specificity in the assay is achieved by using monospecific antibody, oscillators so prepared can be used to independently assay for several different types of proteins, according to the composition of the attached protein layer. Before removing the oscillator from the antigen solution, a water wash is directed into the solution and the oscillator is thoroughly washed without contacting the air. This wash procedure prevents contact of the oscillator with denatured protein at an air-protein solution interface. The oscillator is removed and allowed to dry. The frequency of the coated oscillator is then determined. The oscillator is ready to be used in an immunochemical assay.

The antigen-coated oscillator is stable and may be stored for extended periods of time (e.g. several months) without loss of immunological activity.

A convenient means for carrying out the method of the invention is to provide an immunological diagnostic kit comprising a piezoelectric oscillator precoated with at least one or a combination of antigens to be determined and having a premeasured frequency. In conjunction with the antigen-coated oscillator there is provided a predetermined amount of an antibody specific for the antigen. To carry out the method, the antibody is added to the unknown liquid sample, e.g. blood or urine, and the sample is then contacted with the oscillator. The change in frequency of the oscillator is measured. By reference to a standard curve, the presence of the antigen in the sample and the concentration thereof can be determined.

The method of the present invention may be used to assay for virtually all antigenic materials of clinical interest including naturally occurring and synthetic drugs, drugs of abuse, hormones, vitamins, antibiotics, and the like. Other materials which may be used as antigen coats include tissue-associated proteins such as myoglobin, and $\alpha_2$-microglobin; plasma proteins such as albumin, gamma-globulins (e.g., IgG, IgA, IgM, IgD and IgE), haptoglobin, complement factors, fibrinogen, $\alpha_1$-antitrypsin, and high and low density lipoproteins; organ specific enzymes such as amylase, lactic dehydrogenase and creatinine phosphokinase. Especially preferred antigens include Cohn II gamma globulins, $\alpha$ globulins, serum albumin, thyroxin and amylase.

The invention may be further illustrated by reference to the following examples:

EXAMPLE 1

The Preparation of Piezoelectric Oscillators and the Competitive Assay Method for Human Gamma Globulin (IgG).

Preparation of the Oscillators: 10 MHz (fundamental) AT cut quartz crystal oscillators[1] (0.3 cm diameter) mounted in MIL type HC-6/U holders were surface-treated by soaking overnight in a 0.06% aqueous solution of poly(2-hydroxy-3-dimethylamino-1,4-butane[2]) with stirring at room temperature. The oscillators were washed of excess polymer by flooding with a copious quantity of deionized water and then dried in a stream of nitrogen. After equilibrium at room temperature (50% relative humidity), the base frequency of the oscillators was determined using a Hewlett-Packard model 5300A digital frequency meter attached to the output of an International Crystal OT-13 oscillator circuit. The oscillators thus prepared had a uniform coating of polymer corresponding to a mean change in frequency ($\Delta F$) of 285 Hz per oscillator.
[1]Northern Engineering Laboratories, NE-6.
[2]Prepared according to U.S. Pat. No. 3,740,414

The antigen employed was human gamma globulin (IgG from Cohn Fraction II[3]). A 10 mg/ml solution of the antigen in 0.02 M phosphate buffered saline (PBS, pH 7.0) was prepared and the solution allowed to stand overnight at 4° C. The clear supernatant was decanted and immediately filtered through Whatman No. 1 filter paper. The polymer-treated oscillators were incubated in the Cohn II gamma globulin solution at room temperature, with stirring for 4 hours. The solution was then flooded with PBS, followed by sufficient deionized water to ensure that no adsorbable substances remained in the oscillator-treatment bath. After drying in a nitrogen stream and equilibration at 50% relative humidity, the resultant frequency of each oscillator was determined. The composite Cohn II gamma globulin oscillators had a very uniform amount of protein attached thereto corresponding, in this case, to a $\Delta F$ of 580±63 Hz per oscillator. This frequency change is in addition to that observed with the polymer coating polymer.
[3]Sigma Chemical Company, St. Louis, Missouri

Assay Procedure

The procedure is illustrated by the preparation of a standard curve relating frequency shift to IgG concentration. Since each determination point of the standard curve is essentially an unknown before the assay is performed, the determination of a standard curve can be taken as illustrative of the analysis of unknowns.

An assay mixture was prepared by combining sequentially an aliquot of a commercially prepared human serum standard (Q.I.C. ®)[4,5] containing the antigen which had been diluted 1:10 with phosphate buffered saline, 0.250 ml antihuman IgG (5.0 mg antibody/ml) and sufficient phosphate buffered saline to provide a final volume of 20.0 ml. Three oscillators (prepared as above) were immersed in this assay mixture and incubated 75 minutes at room temperature with stirring. After incubation, the oscillators were recovered by flood rinsing sequentially with phosphate buffered saline and sufficient deionized water to remove all adsorbable species. After drying in a stream of nitrogen and equilibration at 50% R.H. the final frequency of the oscillators was determined.

[4] Quantitative Immunodiffusion Control trademark of Meloy Laboratories, Inc.
[5] For unknown serum samples, 20 microliters of sera would be used.

The loss in frequency for the Cohn II gamma globulin oscillator is directly related to the extent of antibody reaction with the oscillator, and is a measure of excess or unreacted antibody in the assay. Therefore, the frequency shift is *inversely* related to IgG concentration in the samples.

The table below summarizes the results obtained using a commercially prepared serum standard, (Q.I.C. ®) diluted 1:10 with PBS. Mean IgG concentration for the undiluted sample was 8.07 mg/ml.

| $\Delta F$ (Hz, Average) | Q.I.C. ® Aliquot | IgG Concentration In Assay Mixture | Moles/ Liter |
| --- | --- | --- | --- |
| 511 | 0.050 ml | 2 µg/ml | $1.3 \times 10^{-8}$ |
| 561 | 0.100 ml | 4 µg/ml | $2.6 \times 10^{-8}$ |
| 495 | 0.200 ml | 8 µg/ml | $5.3 \times 10^{-8}$ |
| 370 | 0.250 ml | 10 µg/ml | $6.6 \times 10^{-8}$ |
| 165 | 0.300 ml | 12 µg/ml | $8.0 \times 10^{-8}$ |
| 100 | 0.400 ml | 16 µg/ml | $10.6 \times 10^{-8}$ |

EXAMPLE 2

Preparation of Oscillators and the Competitive Assay Technique for Thyroxine (Small Molecule Assays)

Preparation of the Oscillators

10 MHz AT cut quartz crystal oscillators were surface treated as described in Example 1. The antigen employed was L-thyroxine[6] (sodium salt). A 100 µg/ml dispersion of this material in 0.02 M PBS was prepared and incubated by stirring overnight at room temperature with polymer-treated oscillators. Following the procedure of Example 1, a composite L-thyroxine-oscillator was obtained having a very uniform amount of L-thyroxine, corresponding to a $\Delta F$ of $476 \pm 42$ Hz per oscillator.

[6] Sigma Chemical Company

Assay Procedure

The procedure is illustrated by the preparation of a standard curve relating frequency shift to L-thyroxine concentration.

The assay mixture was prepared by mixing sequentially an aliquot of an L-thyroxine standard, 0.100 ml thyroxine standard, 0.100 ml thyroxine antisera (γ-fraction, 10 mg protein/ml) and sufficient phosphate buffered saline (PBS) to provide a final volume of 20.0 ml. The mixture was stirred and incubated 60 minutes at room temperature with two L-thyroxine coated oscillators. After incubation, the oscillators were recovered by flood rinsing consecutively with PBS and sufficient deionized water to remove all adsorbable species. After drying in a stream of nitrogen and equilibration at 50% relative humidity the final frequency of each oscillator was determined.

The table below summarizes the results obtained using aliquots of a thyroxine standard (1.0 mg/ml in 0.02 M PBS, pH 7.0).

| $\Delta F$ (Average) | Thyroxine Aliquot | Thyroxine Conc. in Assay Mixture |
| --- | --- | --- |
| 165 Hz | 0.010 ml | 0.5 ng/ml |
| 137 Hz | 0.050 ml | 2.5 ng/ml |
| 70 Hz | 0.100 ml | 10.0 ng/ml |

EXAMPLE 3

Preparation of Oscillators and the Competitive Assay for Human Serum Albumin Using 5 MHz Oscillators and a Small Reaction Volume 5 MHz AT cut quartz crystal oscillators were surface treated as described in Example 1. Human serum albumin (HSA) was attached to the oscillators by incubating the polymer-treated oscillators at room temperature with HSA solution (7.5 mg/ml, PBS pH 7.0) for 5 minutes. After washing, composite oscillators were obtained having a uniform coating of human serum albumin corresponding to a mean $\Delta F$ of $72 \pm 15$ Hz per oscillator.

Assay Procedure

One milliliter of a solution containing 110 µg/ml antihuman serum albumin[7] in PBS pH 7.0 was rapidly combined with 1.0 ml of a commercially prepared human serum standard (Q.I.C. ®, 40 mg HSA/ml) diluted with PBS to provide HSA concentrations in the range, 0.5–20 µg/ml. Immediately after mixing, 0.5 ml aliquots of this solution were added to individual oscillators and the mixture (oscillators and solution) allowed to incubate at room temperature without stirring for 75 minutes. Each HSA concentration was assayed in triplicate. After incubation the oscillators were recovered by flood rinsing consecutively with pH 7.0 PBS and sufficient deionized water to remove all adsorbable species. After drying in a stream of nitrogen and equilibrium at 50% relative humidity the final frequency of the oscillators was determined.

[7] Meloy Laboratories, Inc.

The table below summarizes the results obtained using a dilute Q.I.C. ® prepared as indicated above.

| $\Delta F$, Average | HSA Concentration In Assay Mixture |
| --- | --- |
| 103 Hz | 0 µg/ml |
| 88.3 Hz | 0.5 µg/ml |
| 69.6 Hz | 4.0 µg/ml |
| 48.0 Hz | 20.0 µg/ml |

EXAMPLE 4

Preparation of Oscillators and a Competitive Assay Using Glutaraldehyde Immobilized Protein

Preparation of Oscillators

A 500 µl aliquot of human γ-globulins, Cohn fraction II (1.0 mg/ml in 0.1 M acetate, pH 5.0) was combined with 25 µl of 1% glutaraldehyde (in 0.1 M acetate, pH 5.0) and the mixture very thinly painted on the electrode portion of 10 MHz AT-cut quartz crystal oscillators. The coated oscillators were kept in a humid atmosphere (water bath) at room temperature for 45 minutes. Excess salt and ungelled protein were removed by soaking 30 minutes in four consecutive changes of distilled water, and the oscillators dried in a stream of nitrogen. After a 15 minute equilibration at ambient temperature and humidity, the resultant frequency of each oscillator was determined. A coating of glutaraldehyde cross-linked γ-globulins corresponding to mean ΔF of 1320 Hz per oscillator was found.

Assay Procedure

A standard curve relating frequency shift to human IgG concentration was obtained following the procedure described in Example 1. Sample volumes utilized were 10 ml for each assay and contained 53.35 μg anti-human IgG/ml. Each point was run in duplicate. The results for a series of aliquots of dilute Q.I.C.® (1:10 with PBS) are given below:

| Q.I.C. ® Aliquot | IgG Concentration In Assay Mixture | ΔF (Hz) |
| --- | --- | --- |
| 0.050 ml | 4 μg/ml | 187.5 |
| 0.100 ml | 8 μg/ml | 137 |
| 0.200 ml | 16 μg/ml | 80.5 |
| 0.300 ml | 24 μg/ml | 74.5 |

EXAMPLE 5

Assay for the Protein IgM Using One Face of the Oscillator at a Time

Piezoelectric oscillators were prepared as described in Example 1 except that incubation time was extended to 24 hours. After washing, a composite oscillator was obtained having a uniform coating of human Cohn fraction II γ-globulins corresponding to a mean ΔF of 1367 Hz per oscillator.

Assay Procedure

The antigen-coated oscillators were mounted horizontally and placed in a petri dish containing a dampened filter paper in order to maintain a high relative humidity during the incubation period. An assay mixture was then prepared by combining, consecutively, 25 μl antihuman IgM, 1.0 ml PBS and a 10 to 50 μl aliquot of undiluted Q.I.C. ®. A 50-60 μl droplet of this mixture was immediately applied to one face of the oscillator in such a manner as to expose the entire electrode surface to the solution. The petri dish was then covered and the oscillator incubated for 75 minutes at room temperature. The droplet was then washed away with a stream of distilled water (about 100 ml). After drying in a stream of nitrogen and equilibrating at 50% relative humidity, the final frequency of the oscillator was determined. The results for a series of aliquots of undiluted Q.I.C. ® are as follows:

| Q.I.C. ® Aliquot | IgM Concentration In Assay Mixture | ΔF |
| --- | --- | --- |
| 0.0 ml | 0 μg/ml | 134 Hz |
| 0.010 ml | 8.8 μg/ml | 113 Hz |
| 0.025 ml | 22.0 μg/ml | 73 Hz |
| 0.050 ml | 44.0 μg/ml | 45 Hz |

A standard curve plotted from this data is shown in FIG. 2.

EXAMPLE 6

Assay for a Protein (α-antitrypsin) in the α-globulin Fraction of Human Sera

Oscillators were prepared as described in Example 1 except that human α-globulin fraction IV was used. A mean ΔF of 320 Hz per oscillator was found.

Assay Procedure

The antigen-coated oscillators were mounted horizontally and placed in a petri dish containing a dampened filter paper to maintain a high relative humidity during the incubation period. An assay mixture was prepared by combining 100λ antisera to human $α_1$-antitrypsin (0.8 mg Ab/ml), 0.5 ml PBS and a 10–200λ aliquot of undiluted Q.I.C. ®. The mixture for each aliquot was vortexed and allowed to stand at room temperature for 30 minutes. A 50λ droplet of each sample was then applied to one face of a previously prepared α-globulin oscillator in such a manner as to expose the entire electrode surface to the solution. The petri dish was then covered and the oscillator incubated for 30 minutes at room temperature. The droplet was then washed away with a stream of distilled water and dried with nitrogen. After equilibrating at ambient humidity, the final frequency of the oscillator was determined. The results for a series of aliquots of undiluted Q.I.C. ® are given in the following table. All aliquots were run in duplicate.

| Q.I.C. ® Aliquot | $α_1$-antitrypsin Concentration (mg/ml) In Assay Mixture | ΔF (Hz) |
| --- | --- | --- |
| 10λ | 30 | 106 |
| 25λ | 73 | 93 |
| 50λ | 146 | 75 |
| 95λ | 250 | 46 |
| 200λ | 457 | 25 |

What is claimed is:

1. A method for the immunochemical determination of at least one antigen in a liquid sample comprising:
   contacting said liquid sample simultaneously with (a) a predetermined quantity of an antibody specific for said antigen being determined; and (b) a composite comprising a piezoelectric oscillator having immobilized thereon in biologically active configuration said antigen or mixture containing said antigen, said composite having a premeasured frequency;
   allowing the immunochemical reaction to proceed;
   removing the oscillator from said liquid sample; and
   measuring the change in frequency of said piezoelectric oscillator.

2. The method according to claim 1 further comprising the step of determining the amount of said antigen in said liquid sample by reference to a standard curve.

3. The method according to claim 1 wherein said piezoelectric oscillator is a 5 to 15 MHz quartz crystal oscillator having plated thereon at least two metal electrodes.

4. The method according to claim 1 wherein said metal electrodes are silver, nickel, gold, chromium or tantalum.

5. The method according to claim 1 wherein said liquid sample is a biological fluid.

6. The method according to claim 5 wherein said biological fluid is serum.

7. The method according to claim 5 wherein said biological fluid is urine.

8. The method according to claim 1 wherein said immobilized antigen is selected from the group consisting of:

tissue-associated proteins, plasma proteins, drugs, vitamins, antibiotics, polysaccharides, hormones and nucleic acids.

9. The method according to claim 8 wherein said antigen is selected from the group consisting of:

Cohn II gamma globulins, α-globulins, serum albumin, thyroxin and amylase.

10. An immunological diagnostic kit for use in a competitive binding assay for the immunochemical determination of at least one antigen in a liquid sample comprising:

a composite comprising a piezoelectric oscillator having immobilized thereon in biologically active configuration an antigen or mixture containing the antigen being determined, said composite having a premeasured frequency; and a predetermined quantity of antibody specific for said antigen being determined.

11. The kit according to claim 10 wherein said piezoelectric oscillator is a 5 to 10 MHz quartz crystal having deposited thereon two metal electrodes.

12. The kit according to claim 11 wherein said metal electrodes are silver.

13. The kit according to claim 10 whrein said antigen is selected from the group consisting of:

tissue-associated proteins, plasma proteins, drugs, vitamins, antibiotics, polysaccharides, hormones and nucleic acids.

14. The kit according to claim 13 wherein said antigen comprises:

Cohn II gamma globulins, α-globulins, serum albumin, thyroxin and amylase.

15. A composite comprising a piezoelectric oscillator having a first layer of poly(2-hydroxy-3-dimethylamino-1,4-butane) on the surface thereof and a second layer of thyroxin immobilized thereon in a biologically active configuration.

* * * * *